US00PP12164P2

(12) United States Plant Patent
Heims

(10) Patent No.: US PP12,164 P2
(45) Date of Patent: Oct. 23, 2001

(54) ***X HEUCHERELLA* PLANT NAMED 'DAYGLOW PINK'**

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/452,027

(22) Filed: Nov. 30, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman Campbell Leigh & Whinston LLP

(57) ABSTRACT

A new and distinct hybrid of *x Heucherella* plant characterized by a unique combination of intense mauve-pink flowers and deeply lobed and dark centered foliage.

1 Drawing Sheet

The present invention relates to a new and distinct intergeneric hybrid of Heuchera and Tiarella, of the family Saxifragaceae. It originated as a cross between an unpatented, unnamed Heuchera hybrid seedling (seed parent) and a plant patent applied for Tiarella named 'Spring Symphony' (pollen parent) (U.S. patent application Ser. No. 09/324,624). Due to the fact that the instant plant and parent plants are the result of crosses between two or more different Heuchera and/or Tiarella species, no species designations are given.

This new *x Heucherella* is a result of a controlled cross of the aforementioned plants of Terra Nova Nurseries, Inc., in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Intense purplish-pink flowers.
2. Deeply lobed and dark centered foliage.

Asexual propagation by division and tissue culture as done by Canby, Oreg., shows that the foregoing characteristics and distinctions come true to form and are established and transmitted through succeeding propagations.

BRIEF DESCRIPTION OF THE DRAWING

The drawing shows *x Heucherella* 'Dayglow Pink' in May in Canby, Oreg.

DETAILED PLANT DESCRIPTION

The following is a detailed description of the new *x Heucherella* hybrid based on observations of two-year old specimens growing in the field in Canby, Oreg. The color descriptions are all based on The Royal Horticultural Society Colour Chart.

Foliage:
- *Type.*—Simple. Semi-evergreen.
- *Shape.*—Cordate. 3-Palmately parted lobes. Individual lobe is cleft.
- *Length.*—10–14 cm.
- *Width.*—8–13 cm.
- *Petiole length.*—14–17 cm.
- *Margins.*—Dentate-crenate. Ciliolate.

- *Apex.*—Broadly acute.
- *Base.*—Cordate.
- *Leaf texture.*—Puberulent. Moderately rugose.
- *Petiole texture.*—Pubescent.
- *Leaf arrangement.*—Rosette.
- *Venation.*—Reticulate.

Size:
- *Height.*—20 cm (2 year old plant grown in Canby, Oreg.).
- *Width.*—47 cm (2 year old plant grown in Canby, Oreg.).

Flower bud:
- *Size.*—Approximately 0.5 cm. long.
- *Shape.*—Oblong, downfacing.

Flower:
- *Type.*—Perfect. Complete.
- *Shape.*—Stellate.
- *Size.*—Grows to 1 cm. wide and 0.4 cm. deep.
- *Petal count.*—5.
- *Petal shape.*—Lanceolate with a clawed base.
- *Petal size.*—0.3 cm. long and less than 0.1 cm. wide.
- *Petal texture.*—Satiny.
- *Calyx count.*—5 lobes divided to ⅔ the way to the pedicel.
- *Calyx shape.*—Campanulate.
- *Calyx size.*—0.6 cm. wide and 0.4 cm. deep.
- *Calyx texture.*—Glandular pubescent.
- *Ovary position.*—Superior.
- *Carpel number.*—2.
- *Stamen number.*—5 with sterile anthers.
- *Inflorescence type.*—Thyrse.
- *Flower number per inflorescence.*—50–100.
- *Peduncle width.*—3–4 mm.
- *Peduncle texture.*—Pubescent.
- *Blooming height.*—48 cm.
- *Bloom period.*—Early April to late May. Sporadic rebloom until fall.
- *Fragrance.*—None.

Fruit:
- *Fertility.*—Sterile, no fruit or seed produced.

Habit: Clumping. Non-stoloniferous.

Disease: None observed on plants grown in Canby, Oreg.

Hardiness: Cold hardy to USDA zone 4. Evergreen in zones 6–8. Deciduous in zones 4 & 5.

Color characteristics:

*Foliage.*—Upper surface.—RHS 143A Green Group becoming RHS 137A–C Green Group with maturity. Upper surface, along veins.—RHS 200A Brown Group. Lower surface.—RHS 147B Yellow-Green Group.

*Flower.*—Bud.—RHS 67C Red-Purple Group. Petal.—RHS 62D Red-Purple Group. Sepal.—RHS 68B Red-Purple Group. Ovary.—RHS 65B Red-Purple Group.

*Peduncle.*—RHS 152A Yellow-Group becoming RHS 184B Greyed-Purple Group from midway up to the apex.

DESCRIPTION OF PARENT PLANTS

The instant plant resulted from a cross between a Heuchera hybrid seedling and Tiarella 'Spring Symphony' PPAF. The Heuchera hybrid seedling was selected as a parent plant for its large pink flowers and strong silver-mottled leaves. The instant plant differs from the Heuchera hybrid seedling in having larger, brighter flowers, palmately parted, dark-centered leaves, and leaf veiling is not obvious. Tiarella 'Spring Symphony' was selected for its intense pink flowers and well-marked compact foliage. The instant plant differs from Tiarella 'Spring Symphony' in having intense mauve-pink flowers, broader lobes, dentate-crenate margins, and larger flower size.

I claim:

1. A new and distinct hybrid of *x Heucherella* plant substantially as shown and described, characterized by a unique combination of intense mauve-pink flowers and deeply lobed and dark centered foliage.

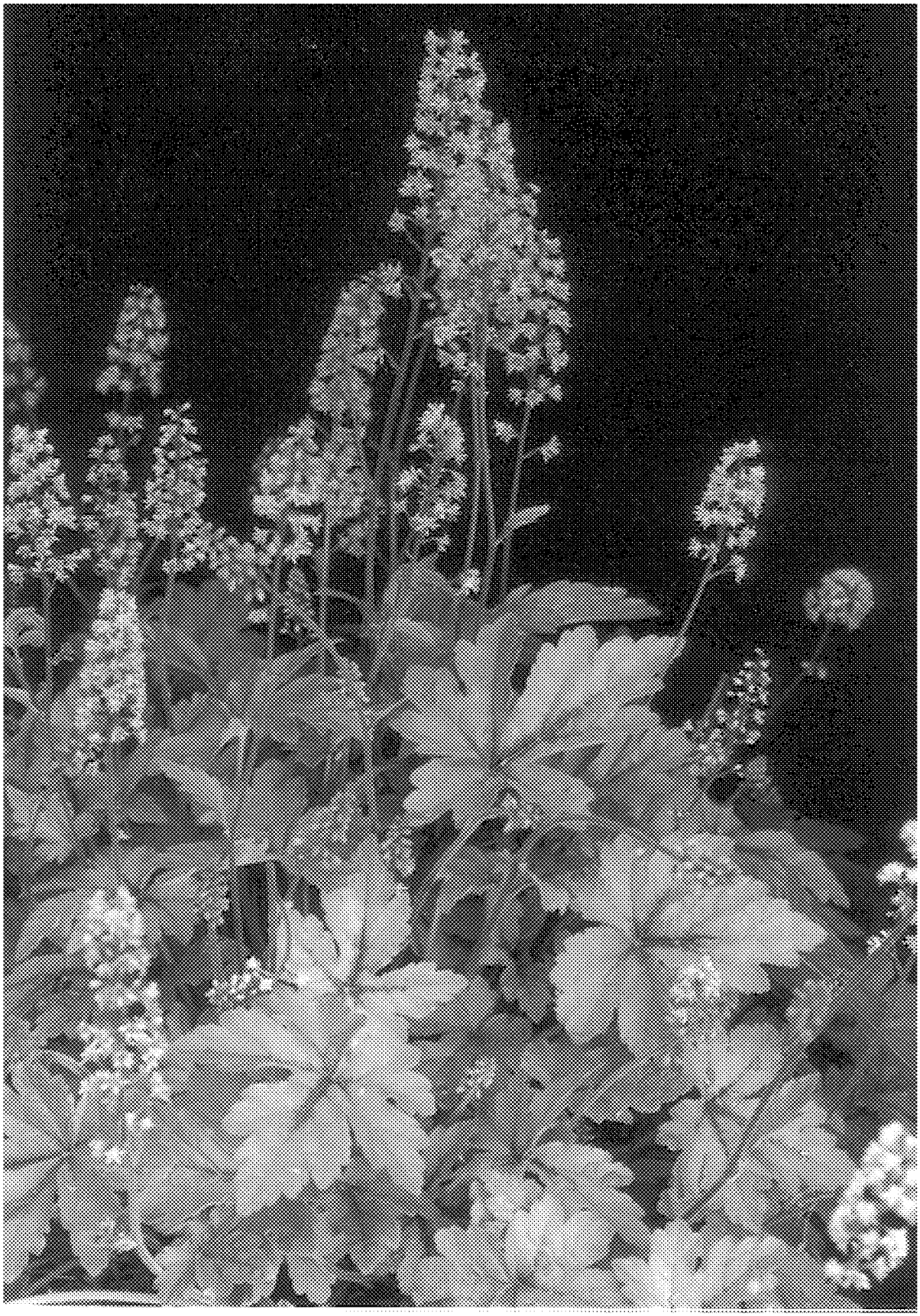

* * * * *